United States Patent [19]
Burklow et al.

[11] Patent Number: 5,902,595
[45] Date of Patent: May 11, 1999

[54] PESTICIDAL COMPOSITION AND METHOD OF USE

[75] Inventors: Eddie R. Burklow, Marietta; Jeffrey S. Kiel, Gainesville, both of Ga.

[73] Assignee: Effcon, Inc., Marietta, Ga.

[21] Appl. No.: 08/901,216

[22] Filed: Jul. 28, 1997

Related U.S. Application Data

[60] Provisional application No. 60/022,377, Jul. 29, 1996.

[51] Int. Cl.⁶ ................................................ A01N 25/02
[52] U.S. Cl. ..................... 424/405; 424/406; 424/70.1; 514/512; 514/703; 514/739
[58] Field of Search .................... 424/405, 406, 424/70.1, 74, 401, 195.1; 514/506, 512, 513, 529, 693, 724, 729, 739

[56] References Cited

U.S. PATENT DOCUMENTS

| | | | |
|---|---|---|---|
| 4,193,986 | 3/1980 | Cox | 424/28 |
| 4,256,600 | 3/1981 | Lewis et al. | 252/132 |
| 4,518,593 | 5/1985 | Juvin et al. | 424/195.1 |
| 4,774,081 | 9/1988 | Flashinski et al. | 424/78 |
| 4,774,082 | 9/1988 | Flashinski et al. | 424/78 |
| 4,906,488 | 3/1990 | Pera | 426/573 |
| 4,999,187 | 3/1991 | Vernon | 424/70 |
| 5,079,000 | 1/1992 | Takahashi et al. | 424/195.1 |
| 5,106,622 | 4/1992 | Sherwood et al. | 424/195.1 |
| 5,227,163 | 7/1993 | Eini et al. | 424/195.1 |
| 5,227,406 | 7/1993 | Beldock et al. | 514/703 |
| 5,298,250 | 3/1994 | Lett et al. | 424/405 |
| 5,346,922 | 9/1994 | Beldock et al. | 514/703 |
| 5,411,992 | 5/1995 | Eini et al. | 514/731 |
| 5,518,736 | 5/1996 | Magdassi et al. | 424/451 |
| 5,565,208 | 10/1996 | Vlasblom | 424/405 |
| 5,621,013 | 4/1997 | Beldock et al. | 514/703 |
| 5,648,398 | 7/1997 | Beldock et al. | 514/703 |
| 5,658,584 | 8/1997 | Yamaguchi | 424/405 |
| 5,776,477 | 7/1998 | Ryder | 424/405 |
| 5,792,465 | 8/1998 | Hagarty | 424/405 |

*Primary Examiner*—Neil S. Levy
*Attorney, Agent, or Firm*—Jones & Askew

[57] ABSTRACT

The present invention provides a pesticidal composition with an extraordinarily lethal effectiveness that can also be used to remove and repel parasites, such as lice. The pesticidal composition preferably contains a cleansing agent and a pesticidal agent such as citronellal, citronellol, citronellyl or a mixture thereof. The composition more preferably utilizes citronellyl acetate as the pesticidal agent. The compositions can be administered topically to humans, animals or any infested areas.

9 Claims, No Drawings

PESTICIDAL COMPOSITION AND METHOD OF USE

CROSS REFERENCE TO RELATED APPLICATION

This application claims priority to U.S. Provisional Patent Application No. 60/022,377, filed Jul. 29, 1996.

FIELD OF THE INVENTION

The present invention relates to pesticidal agents. In particular, the invention relates to pesticidal compositions for cleansing infested individuals and repelling future parasites.

BACKGROUND

Pesticides and insects repellents have long been sought for use against harmful or annoying parasites. Pests such as lice and fleas are irritating and painful to their human and animal hosts, and can also be vectors for other agents of disease. The pesticides and repellents available in the prior art, however, suffer from various deficiencies. Often, compositions provided as insect repellents are not insecticidal. Furthermore, many compositions are either toxic or generally unpleasant to the host. Still others require too many separate active ingredients for efficient production and regulation.

Many synthetic prior art compositions have been proposed as insect repellents, but have later been determined to be unsuitable for safe use by humans. One common active ingredient in prior commercial compositions is N,N-Diethyl-m-toluamide (DEET). However, DEET has recently been associated with causing various undesirable side-effects, such as stinging, damage to mucous membranes, and possibly seizures. In 1989, the Centers for Disease Control issued a cautionary statement regarding the use of DEET. Many other prior art compounds proposed for use as a repellent have proven unsuitable for topical application to humans or other animals due to their toxic or noxious effect on the infested individual.

Various crude oil extracts of certain plants, such as citronella oil obtained from *Cymbopogon citrata,* or eucalyptus oil obtained from *Eucalyptus citriodora,* have been provided in the prior art as pest repellents. However, the oil complex itself is greasy and may have an unpleasant odor, which makes its use undesirable. Furthermore, consistent production of a safe and effective product is difficult, due to varying amounts of constituent compounds within batches of these complex oils and the difficulty of monitoring a large number of components. Therefore, insect repellents containing the whole oil of citronella, for example, are undesirable due to their limited repellency, unpleasant odor and consistency, and unreliable composition of potentially harmful and unnecessary agents.

Most prior art insect repellents are taught to be effective only in specific synergistic compositions. In the art, there has not been recognized a simple but effective pesticidal composition which does not require a combination of excess multiple pesticidal ingredients. There has heretofore not been provided a pesticide in a simple but effective composition that is acceptable for human use.

What is needed in the art is an especially effective pesticidal composition with fewer active components that is easier to consistently produce and monitor. The composition should also be able to cleanse an individual being treated for infestation.

Therefore, it is an object of the present invention to provide a pesticide that is mortally effective against parasites, such as lice. It is further an object to provide a composition that may be used as a cleansing shampoo, soap, cream, lotion or spray. These and other objects of the invention will be apparent to those skilled in the art.

SUMMARY OF THE INVENTION

The present invention provides a pesticidal composition with an extraordinarily lethal effectiveness that can also be used to remove and repel parasites, such as lice, from a host individual. The pesticidal composition preferably contains a cleansing agent and a pesticidal agent such as citronellal, citronellol or citronellyl. The pesticidal composition more preferably comprises a citronellyl salt and a cleansing agent. The compositions can be administered topically to humans, animals or to any infested areas.

DETAILED DESCRIPTION OF THE INVENTION

A "pest," as used in the term "pesticide," is meant to include all parasites, such as arthropods, arachnids, triatomes, insects, bugs, flies, lice, fleas, mites, gnats, nits, Chagas, mosquitoes, and ticks, for example. The composition of the present invention is, therefore, intended to be used against all parasites which succumb to the lethal properties thereof.

The present invention provides a pesticidal composition comprising a cleansing agent and a pesticidal agent comprising citronellal, citronellol or citronellyl in a concentration of at least about 8% v/v. Citronellal, citronellol and citronellyl are available from Elan (Newark, N.J.). In preferred embodiments, the pesticidal agent utilized is citronellyl. In more preferred embodiments, the citronellyl is a salt selected from the group consisting of acetate, butyrate, formate, isobutyrate, phenylacetate, proprionate and valerate. In a more preferred embodiment, the citronellyl salt is acetate.

Pesticidal compositions of the invention containing citronellal, citronellol or citronellyl concentrations of greater than 0.75% v/v show pesticidal activity. As the concentration of the pesticidal agent increases, the lethal effectiveness of the composition, as determined by pesticidal and ovicidal data, also increases. The increasingly unexpected lethal effectiveness of the invention is demonstrated at concentrations of 5%, 7.5%, 8%, 8.5%, 9%, 9.5%, 10%, 10.5%, 11%, 11.5%, 12%, 12.5%, 13%, 13.5%, 14%, 14.5% and 15% v/v.

The invention preferably provides a pesticidal composition wherein the pesticidal agent, for example citronellyl, is in a concentration of between about 8% and 25% v/v, more preferably between about 8% and 15% v/v, and most preferably about 12.5% v/v.

The invention provides that the composition contains a cleansing agent to assist in the removal of unwanted pests and debris. By cleansing agent is meant a composition capable of chelating debris or disrupting hydrophobic suspensions, for example, in order to assist in the removal of pests and ovi. Many well known cleansing agents can be used. The cleansing agent can be a detergent. The detergent can be an aqueous detergent such as Steol CS-230 (also known as Sodium Laureth Sulfate) which is available from Stepan (Northfield, Ill.) or a non-aqueous detergent Cedepal HC (also known as Sodium Lauryl Sulfate) which is also available from Stepan (Northfield, Ill).

The pesticidal composition of the invention can further comprise an alcohol. Preferred alcohols include isopropanol and ethanol, but others can be substituted. It is believed that the presence of an alcohol in the composition increases the composition's pesticidal effectiveness by permeabilizing the outer membrane of the parasite ova thereby allowing the pesticidal agent to penetrate the outer membrane of the ova. Functional substitutes that achieve the same result can be substituted for the alcohol without departing from the scope and spirit of the claims.

The pesticidal composition can further include a carrier agent, an antimicrobial agent, or a pH modifier, for example. In one preferred embodiment, the pesticidal composition comprises a paraben as an antimicrobial agent, an acid as a pH modifier and as a cleansing agent, and water. Methyl paraben and propyl paraben are preferred parabens, but others can be substituted. Acetic acid is a preferred acid, but others can be substituted. In a preferred embodiment, the pesticidal composition further comprises about 1 to 40% w/v isopropyl alcohol, 0.01 to 5% w/v methyl paraben, 0.01 to 5% w/v propyl paraben, 0.01 to 10% w/v acetic acid, 30 to 60% v/v detergent and water q.s.p. 100 g. The pesticidal composition more preferably comprises about 20% w/v isopropyl alcohol, 0.2% w/v methyl paraben, 0.1% w/v propyl paraben, 5.0% w/v acetic acid, 55.5% v/v detergent and water q.s.p 100 g.

The pesticidal composition can further include a viscosity modifier, or an antipruritic agent, for example. In one preferred embodiment, the pesticidal composition further comprises camphor as an antipruritic agent, sodium chloride as a viscosity modifier, methyl paraben and/or propyl paraben as an antimicrobial agent, acetic acid as a pH modifier and cleansing agent, and water. In a preferred embodiment, the pesticidal composition further comprises about 0.01 to 5% w/v camphor and 1 to 10% w/v sodium chloride. The pesticidal composition can comprise about 0.75% w/v camphor, 4.87% w/v sodium chloride, 0.2% w/v methyl paraben, 0.1% w/v propyl paraben, 5.7% w/v acetic acid, 35.14% v/v detergent and water q.s.p 100 g.

The pesticidal composition can further be embodied in a non-aqueous composition. In one embodiment, the pesticidal composition comprises a pesticidal agent, an alcohol, a pH modifier, a detergent, an antimicrobial agent, a non-aqueous solvent, and a detergent. In a preferred embodiment, the pesticidal composition further comprises citronellyl as a pesticidal agent, isopropanol as an alcohol, acetic acid as a pH modifier and cleansing agent, methyl paraben as an antimicrobial agent, propyl paraben as an antimicrobial agent, propylene glycol as a solvent, glycerin as a solvent, and Cedepal HC as a non-aqueous detergent. In a more preferred embodiment, the pesticidal composition further comprises about 12.5% citronellyl acetate, 20% isopropanol, 5% acetic acid, 0.2% methyl paraben, 0.1% propyl paraben, 20% propylene glycol, 15% Cedepal HC and glycerin q.s.

The pesticidal composition can further be embodied in a two component system. In the two component system, two components are prepared and stored separately, and then mixed together at the point of use. The "Active Ingredient Component" comprises an alcohol, a pesticidal agent, an antimicrobial agent and a detergent. The "Diluent Component" comprises a pH modifier and an antimicrobial agent. In a preferred embodiment, the "Active Ingredient Component" further comprises isopropanol as an alcohol, citronellyl acetate as a pesticidal agent, methyl paraben as an antimicrobial agent, propyl paraben as an antimicrobial agent and Steol CS-230 as a detergent, and the "Diluent Component" further comprises glacial acetic acid as a pH modifier and as a cleansing agent, methyl paraben as an antimicrobial agent, propyl paraben as an antimicrobial agent and water as a diluent. In a preferred embodiment, the "Active Ingredient Component" further comprises 14.15% w/v citronellyl acetate, 22.64% w/v isopropanol, 0.2% w/v methyl paraben, 0.1% w/v propyl paraben, and 62.83% w/v Steol CS-230, and the "Diluent Component" further comprises 42.86% w/v glacial acetic acid, 0.2% w/v methyl paraben, 0.1% w/v propyl paraben, and water q.s. In this preferred embodiment, the "Diluent Component" comprises about 11 ⅔% of the combined final product. The combined final product in this most preferred embodiment comprises 12.5% w/v citronellyl acetate, 20% w/v isopropanol, 0.2% w/v methyl paraben, 0.1% w/v propyl paraben, 55.5% w/v Steol CS-230, 5% w/v acetic acid and water q.s. Therefore, the "Active Ingredient Component" and the "Diluent Component" are combined in a ratio of about 7.5 to 1. One skilled in the art can routinely modify the relative concentrations of these components, and accordingly the ratio of their combination, to yield a functional pesticide composition.

To the inventor's knowledge, there has not previously been a recognition of the pesticidal effectiveness of a citronellyl as demonstrated herein. The invention provides that citronellal and citronellol also possess a surprising degree of pesticidal effectiveness. Therefore, the invention contemplates that either citronellal and citronellol may be substituted for citronellyl, or added to the pesticidal agent of the composition.

Without being limited by theory, it is believed that the composition of the present invention is surprisingly effective due to the purification of individual compounds. Citronella oil is a complex mixture containing components which may ordinarily mask the potential effectiveness of the individual pesticidal agents citronellyl, citronellol, and citronellal, as disclosed by the present invention. It also appears that a synergistically beneficial effect is achieved in the compositions of the present invention.

The invention also provides a method of treating an individual having a parasite infestation comprising administering to the infestation an insecticide composition as described above. In particular, the composition of the present invention is effective as an insecticide intended for killing and removing lice from humans. Varied treatment regimens are contemplated as being within the method of treatment provided by this invention. Treatment regimens can vary from a single administration to repeated administrations over long time periods. The various possible treatment regimens would be apparent to one skilled in the art based on the invention disclosed herein and are intended to be encompassed in the scope and spirit of the claims.

The present invention is intended to be administered topically to infested areas of an individual, such as the hair and scalp or pubic areas. The composition is preferably provided in the form of a liquid or solid, such as shampoo, soap, cream, or lotion. The invention contemplates that various other complimentary ingredients can be included, such as an antipruritic agent, a pH modifier, or as a general medium. For example, glycerins, glycols, alcohols, lanolins, aloe vera gel, may be provided in the composition. The preferred compositions are shampoos and soaps containing ingredients capable of assisting in cleansing individuals of the debris of dead parasites.

The composition may also be provided in sun screening, tanning or any other topically applicable products. Other uses of the composition are contemplated, such as a pesticidal spray or fogger for application directly to pests or potentially infested areas. For example, the composition can be provided as a pesticide and cleaning agent for fruits and vegetables. The composition can additionally serve as a repellent for cats, dogs, birds, cattle, or sheep, for example. The composition may also be used as a carpet powder, or as a detergent additive, rinse or spray for clothing, bedding or other fabrics. The composition may also be used as an aerosol bomb or as a room spray. Other such uses would be apparent to one skilled in the art upon contemplating the invention disclosed herein and such uses are intended to be encompassed in the scope and spirit of the claims.

EXAMPLES

EXAMPLE I

Method of Testing the Pediculicidal Activity of a Composition

"The Standard Test Method for Effectiveness of Liquid, Gel, or Cream Insecticides Against Adult Human Lice" was used to determine pediculicidal activity for various compositions of the invention. The test protocol has been published by the American Society for Testing and Materials under the designation E938 - 83 (reapproved 1988) and is hereby incorporated by reference.

Briefly, the test were conducted as follows. Twenty-five (25) adult lice were placed into a vial having a screen bottom. The vial was placed in a container of the composition to be tested which was maintained at a temperature of 32° C. A screened plunger was inserted into the top of the vial containing the lice to ensure that the lice did not float to the surface. The lice were thus submerged in the test composition for a set number of minutes (1, 4 or 10). The lice containing vial was then dipped in distilled water maintained at a temperature of 32° C. and gently agitated for one minute. The lice were then gently washed by a stream of 32° C. distilled water. Excess water was removed by blotting with paper toweling.

The lice were then placed on a dark patch and incubated at 31.7° C. and 60% RH. At one and twenty-four hours after treatment, the lice were tested to determine if they would move towards a 37° C. patch. Lice not dead, morbid or moribund will move towards the 37° C. patch. "Morbid" refers to a louse which is unable to move towards heat one hour after treatment; the louse is sickly, but not necessarily dying. A "morbid" louse may recover by twenty-four hours after the treatment. "Moribund" refers to a louse unable to move towards heat twenty-four hours after treatment; the louse is dead or dying. Those lice that were dead or moribund at twenty-four hours were counted as mortalities.

Mortality percentages were corrected by Abbott's Formula. The percent of mortality in a control was subtracted from the percent mortality in the test and then divided by the percent mortality in the test.

EXAMPLE II

Method of Testing the Ovicidal Activity of a Composition

The "Standard Test Method for Determining the Effectiveness of Liquid, Gel, Cream, or Shampoo Insecticides Against Human Louse OVA" was used to determine the ovicidal activity of various compositions of the invention. This protocol was published by the American Society for Testing and Materials as designation: E5117 - 93 and is hereby incorporated by reference.

Briefly, each test was conducted as follows. Thirty human louse eggs attached to human hair cuttings were used for each test condition. The human hair cuttings were affixed to a wood applicator stick and then immersed in the composition to be tested for ten minutes. The test composition was maintained at 32° C. The eggs were then washed by vigorously moving the stick up and down in 32° C. tap water for one minute. A wash bottle was then used to further wash the eggs with 32° C. tap water for an additional minute.

The eggs were then incubated until all eggs exposed to control conditions hatched (approximately 12 days). All eggs were then observed for hatching. Eggs that failed to hatch were recorded as mortalities.

Mortality percentages were corrected by Abbott's Formula. The percent of mortality in a control was subtracted from the percent mortality in the test and then divided by the percent mortality in the test.

EXAMPLE III

Production of Pesticidal Compositions Utilizing Citronellal, Citronellol and Citronellyl The following components were combined in approximate relative amounts to make Formulas A–C.

| citronellyl acetate | | |
|---|---|---|
| Formula A | 0.75% | v/v |
| Formula B | 0.0% | v/v |
| Formula C | 0.0% | v/v |
| citronellal | | |
| Formula A | 0.0% | v/v |
| Formula B | 0.75% | v/v |
| Formula C | 0.0% | v/v |
| citronellol | | |
| Formula A | 0.0% | v/v |
| Formula B | 0.0% | v/v |
| Formula C | 0.75% | v/v |
| synthetic camphor | 0.75% | w/v |
| sodium chloride | 4.87% | w/v |
| methyl paraben | 0.2% | w/v |
| propyl paraben | 0.1% | w/v |
| acetic acid | 5.7% | v/v |
| Steol CS-230 | 36.55% | v/v |
| purified water | q.s. | |

All mixing steps described herein were performed with an explosion proof air driven mixer. The acetic acid was transferred into a mixing vessel. The citronellyl acetate and camphor were added separately, each being mixed until completely uniform. The detergent Steol CS-230 was transferred into a second mixing vessel. While mixing, the acetic acid phase is added to the detergent and mixed thoroughly. In a third vessel, the sodium chloride is dissolved in purified water. This solution was then transferred to the second mixing vessel, and thoroughly mixed. The methyl paraben and propyl paraben were then added while mixing. The final product was poured through a polish filter.

The compositions produced by Formulas A–C demonstrated only slight ovicidal activity when tested for ovicidal activity as described in Example II. The compositions produced by Formulas A–C exhibited 0.3%, 3.4% and 1.2% ovicidal activity, respectively.

EXAMPLE IV

Production of Pesticidal Compositions Containing Citronellal

The following components were combined in approximate relative amounts to make Formulas A–F.

| Citronellal | | |
|---|---|---|
| Formula A | 0.75% | v/v |
| Formula B | 2.5% | v/v |
| Formula C | 5.0% | v/v |
| Formula D | 7.5% | v/v |
| Formula E | 10.0% | v/v |
| Formula F | 12.5% | v/v |
| Synthetic Camphor | 0.75% | w/v |
| Sodium Chloride | 4.87% | w/v |
| Methyl Paraben | 0.2% | w/v |
| Propyl Paraben | 0.1% | w/v |
| Acetic Acid | 3.65% | v/v |
| Steol CS-230 | 36.55% | v/v |
| Purified Water | q.s. | |

All mixing steps described herein were performed with an explosion proof air driven mixer. The acetic acid was transferred into a mixing vessel. The citronellal and camphor were added separately, each being mixed until completely uniform. The detergent Steol CS-230 was transferred into a second mixing vessel. While mixing, the acetic acid phase is added to the detergent and mixed thoroughly. In a third vessel, the sodium chloride is dissolved in purified water. This solution was then transferred to the second mixing vessel, and thoroughly mixed. The methyl paraben and propyl paraben were then added while mixing. The final product was poured through a polish filter.

The compositions produced by Formulas E and F were tested for ovicidal activity as described in Example II. The composition produced by Formula E showed 3.5% ovicidal activity and the composition produced by Formula F showed 0.0% ovicidal activity. The compositions produced by Formulas A–E were tested for pediculicidal activity as described in Example I. They demonstrated pediculicidal activities of 1.5%, 15.7%, 10.9%, 17% and 100%, respectively.

EXAMPLE V

Production of Pesticidal Composition Containing Citronellyl

The following components were combined in approximate relative amounts to make Formulas A–C.

| Citronellyl Acetate | | |
|---|---|---|
| Formula A | 8.9% | v/v |
| Formula B | 10.0% | v/v |
| Formula C | 12.5% | v/v |
| Synthetic Camphor | 0.75% | w/v |
| Sodium Chloride | 4.87% | w/v |
| Methyl Paraben | 0.2% | w/v |
| Propyl Paraben | 0.1% | w/v |
| Acetic Acid | | |
| Formula A | 3.65% | v/v |
| Formula B | 3.65% | v/v |
| Formula C | 5.0% | v/v |
| Steol CS-230 | 36.55% | v/v |
| Purified Water | q.s. | |

All mixing steps described herein were performed with an explosion proof air driven mixer. The acetic acid was transferred into a mixing vessel. The citronellyl acetate and camphor were added separately, each being mixed until completely uniform. The detergent Steol CS-230 was transferred into a second mixing vessel. While mixing, the acetic acid phase is added to the detergent and mixed thoroughly. In a third vessel, the sodium chloride is dissolved in purified water. This solution was then transferred to the second mixing vessel, and thoroughly mixed. The methyl paraben and propyl paraben were then added while mixing. The final product was poured through a polish filter.

The compositions produced by Formulas B and C were tested for ovicidal activity as described in Example II. The compositions produced by both Formulas showed 0.0% ovicidal activity. The compositions produced by Formulas A–C were tested for pediculicidal activity as described in Example I. They demonstrated pediculicidal activities of 97.0%, 100.0% and 100.0%, respectively.

EXAMPLE VI

Production of Pesticidal Compositions Containing an Alcohol

The following components were combined in approximate relative amounts to produce a pesticidal composition containing an alcohol.

| Citronellyl Acetate | 12.5% | v/v |
|---|---|---|
| Synthetic Camphor | 0.75% | w/v |
| Acetic Acid | 6.0% | v/v |
| Alcohol | | |
| Isopropanol | | |
| Formula A | 0.0% | v/v |
| Formula B | 0.0% | v/v |
| Formula C | 20.0% | v/v |
| Formula D | 30.0% | v/v |
| Ethanol | | |
| Formula A | 20.0% | v/v |
| Formula B | 30.0% | v/v |
| Formula C | 0.0% | v/v |
| Formula D | 0.0% | v/v |
| Steol CS-230 | 46.0% | v/v |
| Methyl Paraben | 0.2% | w/v |
| Propyl Paraben | 0.1% | w/v |
| purified water | q.s. | |

The alcohol was transferred into a mixing vessel. The camphor was added to this vessel and mixed until completely dissolved. The methyl and propyl parabens were added next and mixed until fully dissolved. The citronellyl acetate was added and mixed until completely uniform. The acetic acid was added to the vessel and mixed until completely uniform. The Steol CS-230 was added and mixed until completely uniform. Sufficient water was then added to bring the composition to its target weight.

The compositions produced by Formulas A–D demonstrated high levels of ovicidal activity when tested according to the protocol described in Example II. The compositions produced by Formulas A–C showed 100.0% ovicidal activity and the composition produced by Formula D shows 99.3% ovicidal activity.

EXAMPLE VII

Production of Pesticidal Compositions Containing Citronellol

The following components were combined in approximate relative amounts according to Formulas A and B to produce pesticidal compositions containing citronellol.

| | | |
|---|---|---|
| Citronellol | 12.5% | v/v |
| Alcohol | | |
| Isopropanol | | |
| Formula A | 0.0% | v/v |
| Formula B | 20.0% | v/v |
| Ethanol | | |
| Formula A | 20.0% | v/v |
| Formula B | 0.0% | v/v |
| Synthetic Camphor | 0.75% | w/v |
| Methyl Paraben | 0.2% | w/v |
| Propyl Paraben | 0.1% | w/v |
| Acetic Acid | 6.0% | v/v |
| Steol CS-230 | 46.0% | v/v |
| Purified Water | q.s. | |

The alcohol was transferred into a mixing vessel. The camphor was added to this vessel and mixed until completely dissolved. The methyl and propyl parabens were added next and mixed until fully dissolved. The citronellol was added and mixed until completely uniform. The acetic acid was added to the vessel and mixed until completely uniform. The Steol CS-230 was added and mixed until completely uniform. Sufficient water was then added to bring the composition to its target weight.

The compositions produced by Formulas A and B showed 100.0% ovicidal activity.

EXAMPLE VIII

Production of a Non-Aqueous Pesticidal Compositions

The following ingredients were combined in approximate relative amounts to produce a non-aqueous pesticidal composition.

| | | |
|---|---|---|
| Citronellyl Acetate | 12.5% | v/v |
| Isopropanol | 20.0% | v/v |
| Acetic Acid | 5.0% | v/v |
| Propylene Glycol | 20.0% | v/v |
| Methyl Paraben | 0.2% | w/v |
| Propyl Paraben | 0.1% | w/v |
| Cedepal HC | 15.0% | v/v |
| Glycerin | q.s. | |

The methyl and propyl parabens were dissolved in the isopropanol in a mixing vessel. The citronellyl acetate was added to this vessel and mixed until completely uniform. The acetic acid was added next and mixed until completely uniform. Next, the Cedepal HC was added to the vessel and mixed until completely uniform. The propylene glycol was then added and mixed until completely uniform. Finally, glycerin was added to bring the mixture to its target weight.

This composition demonstrated 13.0% ovicidal activity when tested as by the procedure in Example II.

EXAMPLE IX

Production of a Non-Aqueous Pesticidal Composition with a Conditioner Base

The following ingredients were combined in approximate relative amounts to produce a non-aqueous cream rinse formulation.

| | | |
|---|---|---|
| Citronellyl Acetate | 12.5% | v/v |
| Isopropanol | 20.0% | v/v |
| Acetic Acid | 5.0% | v/v |
| Methyl Paraben | 0.2% | w/v |
| Propyl Paraben | 0.1% | w/v |
| Amidox L-5 | 4.0% | v/v |
| Ammonyx 4002 | 8.4% | v/v |
| Cedepal HC | q.s. | |

The Ammonyx 4002, a conditioner available from Stepan (Northfield, Ill.), and the methyl and propyl parabens were completely dissolved in the isopropanol in a mixing vessel. The citronellyl acetate was added to the vessel and mixed until completely uniform. Next, Amidox L-5, a foamer available from Stepan (Northfield, Ill.), was dissolved into the mixture. Finally, the Cedepal HC was added to bring the mixture to its target weight and mixed until uniform.

This pesticidal composition exhibited an ovicidal activity of 12.0% when tested according to the procedure of Example II.

EXAMPLE X

Production of a Two Component Pesticidal Composition

Compositions that were aqueous and contained higher levels of acetic acid (about 5%) displayed high ovicidal activity. However, citronellyl acetate degraded over time in compositions containing both acetic acid and water. Two component pesticidal compositions were therefore developed. Each component of the compositions was produced and stored separately. The two components were mixed at the point of use. The first component was an "Active Ingredient Component" and the second component was a "Diluent Component." One such two component pesticidal composition was prepared in the following manner.

The following ingredients were combined in approximate relative amounts to make the "Active Ingredient Component."

| | | |
|---|---|---|
| Citronellyl Acetate | 14.15% | v/v |
| Isopropanol | 22.64% | v/v |
| Methyl Paraben | 0.2% | w/v |
| Propyl Paraben | 0.1% | w/v |
| Steol CS-230 | 62.91% | v/v |

The isopropanol and the methyl and propyl parabens were mixed in a mixing vessel until the parabens were completely dissolved. The resulting isopropanol/parabens solution was transferred to a second mixing vessel. Steol CS-230 was added to the second mixing vessel and mixed until completely uniform. The citronellyl acetate was added to this vessel and mixed until uniform. The resulting solution was diluted to its final target weight by the addition of Steol CS-230.

The following ingredients were combined in approximate relative amounts to produce the "Diluent Component."

| | | |
|---|---|---|
| Glacial Acetic Acid | 42.86% | v/v |
| Methyl Paraben | 0.2% | w/v |
| Propyl Paraben | 0.1% | w/v |
| Purified Water | q.s. | |

The specified amount of purified water was added to a mixing vessel. The glacial acetic acid was added to the mixing vessel and mixed until completely uniform. The methyl and propyl parabens were added o the mixing vessel and mixed until completely dissolved. The resulting solution was diluted to the final target weight with purified water.

The two components were mixed together at the point of use in relative amounts such that the "Diluent Component" comprised approximately 11 ⅔% of the final combined product. The final product contained the following ingredients in the approximately relative amounts listed below.

| Citronellyl Acetate | 12.5% | v/v |
|---|---|---|
| Isopropanol | 20.0% | v/v |
| Methyl Paraben | 0.2% | w/v |
| Propyl Paraben | 0.1% | w/v |
| Steol CS-230 | 55.5% | v/v |
| Glacial Acetic Acid | 5.0% | v/v |
| Purified Water | q.s. | |

The final combined product of this two component pesticidal composition displayed 100.0% ovicidal activity when tested under the conditions described in Example II.

EXAMPLE XI

Assay for Citronellyl Acetate

In order to test the stability of citronellyl acetate in various pesticidal compositions, the following assay was utilized. This assay utilized a reversed phase high performance liquid chromatography (HPLC) procedure. Two standard solutions were prepared by dissolving 141.5 mg of citronellyl acetate in approximately 20 ml of a 25% water/75% acetonitrile solution. The column was calibrated using these standards. Agreement between the two standards within 3% was considered acceptable.

The standard was then injected into the column five times. The average and the percent relative standard deviation (% RSD) of the peak was calculated. A % RSD of 3% or less was considered acceptable.

One gram of the test composition was then placed into 100 ml volumetric flask and brought to volume with the solution 25% water/75% acetonitrile. An aliquot from the resulting solution was then filtered through a 0.45 PP filter and injected into the HPLC column. Each sample preparation was tested twice and a standard was run on the column after every two test injections.

The concentration of citronellyl acetate was calculated for each test composition by dividing the peak response of the sample by the peak response of the standard and multiplying the result by the sample weight factor and the assay standard concentration in % Label Claim.

The following ingredients were combined in approximate relative amounts to produce pesticidal compositions with Formula A–K and were tested with this assay. The compositions were produced using the same procedures and basic ingredients as the compositions described in the preceding Examples. The key ingredients were as follows. Formulas A–J contained 12.5% citronellyl acetate and Formula K contained 12.5% citronellol. All Formulas contained 20.0% isopropanol. Formulas A–F and Formulas J and K contained 55.0% Steol CS-230 and water. Formulas G–I did not contain water and Formulas H and I contained 4.0% Ammonyx. Formula I also contained 6.0% Stepanol WA100 and 1.8% Amidox. Formula J was titrated to a pH of 3.5 with 1N HCl. Formula A contained no acid. Formulas B–I and Formula K contained varying amounts of acetic acid as listed below.

| Formula | Acetic Acid Concentration |
|---|---|
| B | 0.1% |
| C | 1.0% |
| D | 2.0% |
| E | 3.0% |
| F | 5.0% |
| G | 5.0% |
| H | 5.0% |
| I | 5.0% |
| K | 5.0% |

The initial citronellyl acetate concentration for each composition tested was determined using the above-described assay. Compositions produced from Formulas A, B and F were stored at room temperature, 40° C. (accelerated standard temperature) and 60° C. The compositions stored at 60° C. were assayed for active citronellyl acetate after two weeks. The compositions stored at room temperature and at 40° C. were assayed for active citronellyl acetate at one and two months. Compositions produced according to Formulas C, D, E, G, H, J and K were stored for two weeks at 60° C. and assayed for active citronellyl acetate.

The results of these assays are presented in the following table.

Percent Of Citronellyl Acetate (Active)

| Formula | Initial | 60¤ 2 weeks | Room Temperature 1 month | Room Temperature 2 months | Accelerated Standard Temperature (40¤ C.) 1 month | Accelerated Standard Temperature (40¤ C.) 2 months |
|---|---|---|---|---|---|---|
| A | 98.0 | 85.8 | 94.5 | 98.3 | 94.0 | 95.2 |
| B | 97.4 | 82.3 | 93.9 | 96.2 | 91.2 | 91.7 |
| C | 92.4 | 53.4 | | | | |
| D | 93.6 | 25.0 | | | | |
| E | N/A | 45.8 | | | | |
| F | 94.0 | 29.8 | 88.6 | 88.7 | 77.3 | 71.2 |
| G | 94.7 | N/A | | | | |
| H | 94.2 | 88.6 | | | | |
| J[1] | 90.6 | 6.2 | | | | |
| K | 86.0 | 68.1 | | | | |

[1]No results are available for Formula I.

The Examples above are intended to be demonstrative, but not exhaustive, of the embodiments contemplated by the present invention. It is intended that other deviations apparent to those skilled in the art from the invention described above are encompassed in the scope and spirit of the claims.

What is claimed is:

1. A method of killing lice and their ovi comprising topically administering to a lice infestation a pesticidal and ovicidal composition comprising an aqueous detergent, an alcohol selected from the group consisting of ethanol and isopropanol, and a pesticidal and ovicidal agent selected from the group consisting of citronellal, citronellol, citronellyl and combinations thereof, wherein the pesticidal and ovicidal agent is in a concentration of at least about 8%, v/v, and wherein the composition is non-noxious to humans and has greater than 13% pesticidal and ovicidal activity as determined by ASTM E938-83 and E5117-93, respectively.

2. The method of claim 1, wherein the pesticidal agent is citronellyl.

3. The method of claim 2, wherein the citronellyl is a salt selected from the group consisting of acetate, butyrate, formate, isobutyrate, phenylacetate, proprionate and valerate.

4. The method of claim 3, wherein the citronellyl salt is acetate.

5. The method of claim 2, wherein the citronellyl is in a concentration of between about 8% and 25% v/v.

6. The method of claim 5 wherein the citronellyl is in a concentration of about 10% to 20% v/v.

7. The method of claim 1, wherein the composition further comprises an antipruritic agent.

8. The method of claim 2 wherein the composition further comprises a pH modifier, an antimicrobial agent, or a viscosity modifier.

9. The method of claim 1, wherein the infestation is on a mammal.

* * * * *